(12) United States Patent
Weibel

(10) Patent No.: US 7,576,863 B2
(45) Date of Patent: Aug. 18, 2009

(54) HORIZONTAL SURFACE PLASMON RESONANCE SENSOR APPARATUS

(75) Inventor: Stephen C. Weibel, Madison, WI (US)

(73) Assignee: GWC Technologies, Inc., Madison, WI (US)

( * ) Notice: Subject to any disclaimer, the term of this patent is extended or adjusted under 35 U.S.C. 154(b) by 0 days.

(21) Appl. No.: 12/018,518

(22) Filed: Jan. 23, 2008

(65) Prior Publication Data

US 2008/0198383 A1 Aug. 21, 2008

Related U.S. Application Data

(60) Provisional application No. 60/889,961, filed on Feb. 15, 2007.

(51) Int. Cl.
*G01N 21/00* (2006.01)
(52) U.S. Cl. ........................................ 356/445
(58) Field of Classification Search .......... 356/445–448
See application file for complete search history.

(56) References Cited

U.S. PATENT DOCUMENTS 7,265,844 B2 * 9/2007 Codner et al. ............... 356/445

* cited by examiner

*Primary Examiner*—Michael P Stafira
(74) *Attorney, Agent, or Firm*—Alan R. Stewart; Brian G. Gilpin; Godfrey & Kahn, S.C.

(57) ABSTRACT

Disclosed is a horizontal SPR sensor apparatus that provides a simplified beam path, ease of sample handling with concomitant ease of analysis. The horizontal SPR device disclosed herein includes an input and output transfer mirror pair that translates vertically along an axis perpendicular to the beam path. The invention includes an input/output scanner mirror pair that is operatively linked to the transfer mirror pair. This allows for rotation of the scanner mirror pair in response to the vertical translation of the transfer mirror pair and maintains the incident light focus on the metal film/sample layer while varying the angle of incidence and thereby exciting the surface plasmon resonance at the thin metal film layer. Further, this allows the detector and detector optics to be fixed providing for the implementation of heavier multistage cooled detectors. Finally, the invention provides an SPR device having a smaller footprint than known alternatives.

10 Claims, 10 Drawing Sheets

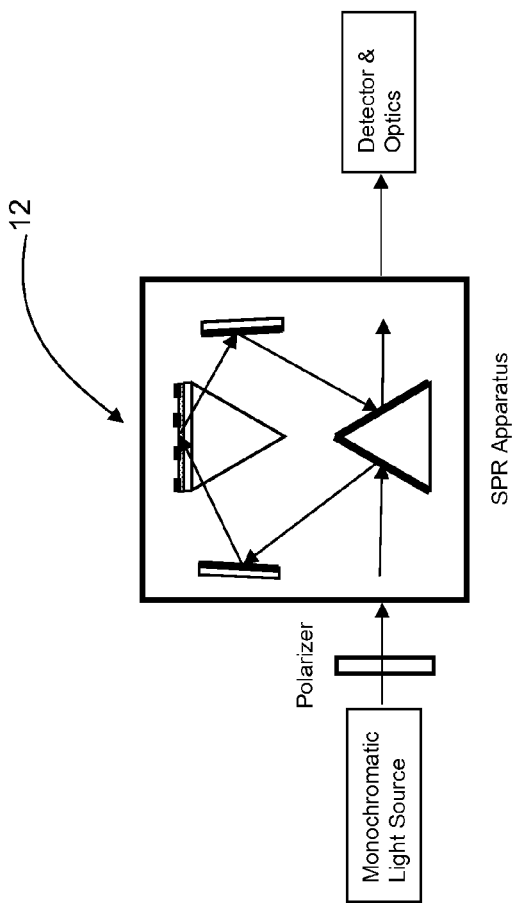

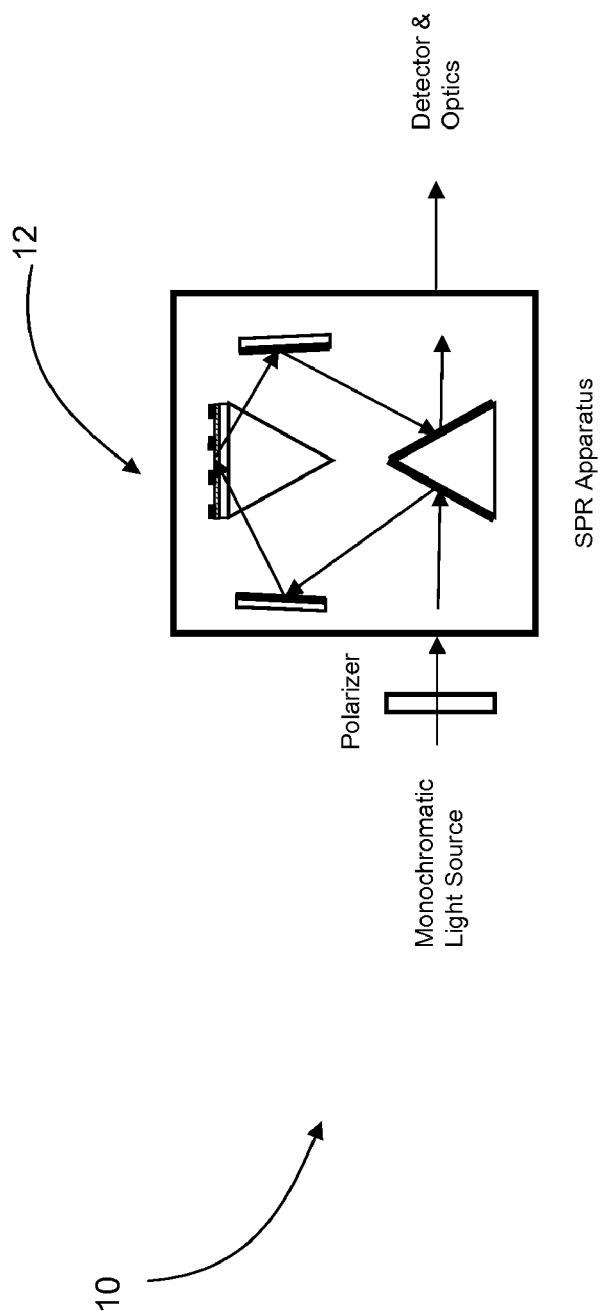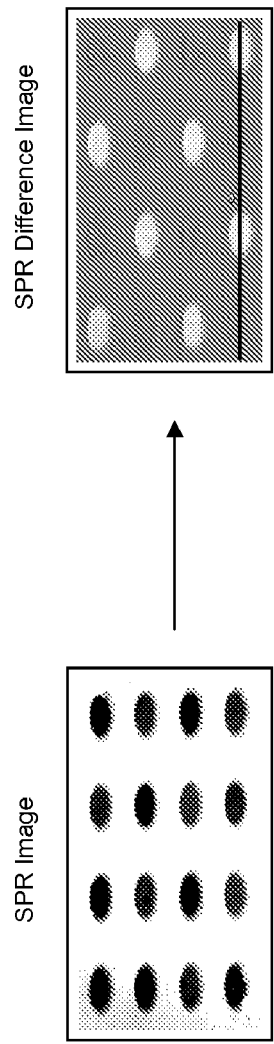

HORIZONTAL SURFACE PLASMON RESONANCE SENSOR APPARATUS

CROSS-REFERENCE TO RELATED APPLICATION

The present application claims priority to U.S. Provisional Application Ser. No. 60/889,961, filed on Feb. 15, 2007, the disclosure of which is incorporated herein by reference.

FIELD OF THE INVENTION

This invention is generally directed to an apparatus for measuring the surface plasmon resonance of a sample. More particularly, the surface plasmon resonance apparatus described herein has a horizontal orientation.

BACKGROUND OF THE INVENTION

This invention is directed to an instrument for making chemical and biological analyses of a sample using surface plasmon resonance. Surface plasmon resonance (SPR) is a method whereby surface plasmons or surface electromagnetic waves, that are characteristic of conducting metal surfaces, are propagated parallel to a metal/dielectric interface. This phenomenon is accomplished in the IR-visible wavelength region for air/metal and water/metal interfaces. In one simple form, SPR reflectivity measurements can be used to detect and identify unknown molecules such as DNA or proteins by the changes in the local index of refraction upon adsorption of the target molecule to the metal surface.

Surface plasmon resonance (SPR) is used in the nondestructive study of surfaces, interfaces, and very thin layers, and has recently been found to be particularly adapted for the study of immunologic phenomenon such as antigen-antibody reactions and protein-protein interactions. A surface plasmon is an oscillation of free electrons propagated along the surface of a conductor which is typically in the form of a thin metal film of gold, silver or copper. Transverse-magnetic (TM) polarized energy in an evanescent field excites surface plasmons on the thin metal film. The characteristics of the resonance are directly related to the refractive indices of materials on both sides of the metal film. By including the sample to be measured as a layer on one side of the metal film, changes in the refractive index of the sample can be monitored by measuring changes in the surface plasmon resonance response. Measurement of the SPR response is done by monitoring the characteristics of reflected light at incident angles above the critical angle.

The surface selectivity of SPR arises from the enhancement of the optical electric fields at metal surfaces when surface plasmon polaritons (SPPs) are created at the metal/dielectric surface. SPPs are coupled photon-plasmon surface electromagnetic waves that propagate parallel to the metal/dielectric interface. The intensity of the optical electric fields associated with an SPP decays exponentially in distance away from the metal surface, with a typical decay length for an SPP into the dielectric being on the order of 200 nm. SPPs cannot be created on an isolated planar metal surface, but rather require a prism or grating coupling geometry for exciting SPPs. Thus, surface plasmon resonance is achieved by using the evanescent wave which is generated when a p-polarized light beam is totally internally reflected at the boundary of a medium having a high dielectric constant, such as glass. The free electron oscillation is affected by the refractive index of the material adjacent the metal surface which forms the basis of SPR measurements.

In a typical SPR scanning angle experiment, p-polarized light from a laser is directed through a prism onto a metal film on which is disposed a thin sample layer being studied. The prism-sample assembly is mounted to a rotation stage, which allows scanning of the incident angle of the laser beam. As the angle of incidence of the laser beam is varied, surface plasmon resonance is evidenced as a sharp dip in the intensity of the laser beam internally reflected within the prism at a particular angle of incidence. The angle of incidence at which resonance occurs is affected by the refractive index of the thin sample layer disposed on the metal film. The angle of incidence corresponding to resonance is thus a direct measure of the characteristics of the thin sample layer. In the case of immunoassays, the measured angle of incidence corresponding to resonance represents a direct measure of the state of reaction between an antibody and its antigen.

A typical SPR instrument employs a method of varying the incident light angle and detecting the internally reflected light by using a $\theta$-$2\theta$ mechanical stage. The classical $\theta$-$2\theta$ mechanical stage has a fixed input light source, a rotating optical element with $\theta$ motion, and a tracking detector stage with $2\theta$ motion. In the prism SPR configuration, as the angle of incidence is varied by rotating the prism optical element x degrees, the detector must rotate 2x degrees to track the beam. Many SPR systems are constructed using this method. FIG. 1 shows the typical layout of such a system.

While the information determined using typical SPR is immense, there are several disadvantages of a system with this type of $\theta$-$2\theta$ stage. Such disadvantages include: the SPR sensor chip is in a vertical or other non-horizontal format making experimental access more difficult; the prism and SPR chip optical elements are on the rotating platform resulting in a non-rigid mount, causing optical instability; the heater control is more difficult to implement because of a rotating non-rigid platform; tracking detector is on a pivot arm that is a moveable non-rigid structure; the detector and detector optics mass require significant torque to rotate; and a gearbox or synchronous rotating stages are required, with resultant mechanical backlash.

Codner et al. described a horizontal SPR instrument in U.S. patent application Ser. No. 10/602,243. While Codner et al. describe a horizontal SPR apparatus that provides for a horizontal SPR surface orientation, this apparatus requires a complex coordination of upper and lower mirrors in relation to the prism and the sample. In order to accomplish this task, the device taught by Codner requires a four-bar linkage system to maintain the beam path as the light is scanned along the sample surface. This design provides a fixed and horizontal SPR chip orientation, however, with a four-mirror system with complex and interacting degrees of freedom resulting in a mechanically complex apparatus.

Similarly, Codner et al. describe a portable SPR instrument in U.S. patent application Ser. No. 10/411,583 (the '583 application) that is designed to provide a device that is smaller, easily transported and can be used outside of the laboratory. However, in order to provide the smaller footprint and portability the device described in the '583 application requires the light source and imaging detector be supported on linked swing arms, limiting the angular range of travel and restricting the type and size of components utilized in the light source and detector assemblies.

Due to these deficits, it would be desirable to have a surface plasmon resonance apparatus that has a fixed input light source, a fixed prism element with horizontally orientated SPR chip attached, with a fixed detector stage allowing for a more compact and less complex apparatus that still provides the versatility of light source and detector systems as larger more complex models.

SUMMARY OF THE INVENTION

Disclosed is a horizontal SPR sensor apparatus or device that provides a simplified beam path, ease of sample handling with concomitant ease of analysis. The horizontal SPR apparatus disclosed herein includes an input and output transfer mirror pair that translates vertically along an axis perpendicular to the beam path. The invention includes an input/output scanner mirror pair that is operatively linked to the transfer mirror pair. This allows for rotation of the scanner mirror pair in response to the vertical translation of the transfer mirror pair and maintains the incident light focus on the metal film/sample layer while varying the angle of incidence and thereby exciting the surface plasmon resonance at the thin metal film layer. Further, this allows the detector and detector optics to be fixed providing for the implementation of heavier multi-stage cooled detectors. Finally, the invention provides an SPR apparatus having a smaller footprint than known alternatives.

In one exemplary embodiment, the invention provides an SPR instrument having a horizontal orientation including an input transfer optics generating a light beam along a beam axis; an input transfer mirror joined to an output transfer mirror and translatable vertical to the beam axis, wherein the input transfer mirror and the output transfer mirror form congruent angles along the axis of symmetry; a first scanner mirror rotatable about an axis and wherein the first scanner mirror directs the beam to a metal film/sample array; a second scanner mirror rotatable about a second rotational axis and receiving light reflected from the metal film/sample array and directing the light to the output transfer mirror; and a detector receiving light from the output transfer mirror; whereby the surface plasmon resonance of a sample is measured.

In some exemplary embodiments of the invention, the input transfer mirror and the output transfer mirror are translationally joined at coequal angles around the axis of symmetry such that the angle of the input beam equals the angle of the output beam. In other exemplary embodiments, the input scanner mirror and the output scanner mirror are symmetrically opposable. In various exemplary embodiments, the light source can be a broadband filament, laser, light emitting diode, FT-IR spectrometer, fiber optic light source or AOTF spectrometer. In some preferred embodiments, the detector is a single element sensor, an imaging detector or an element array detector. In still other embodiments, the detector includes a charged-coupled device camera and a central processing unit.

This invention also provides a method of identifying inter-molecular interaction comprising the steps of placing a target molecule on a probe in a horizontally oriented SPR device; directing a light beam to an input path in the horizontally-oriented SPR device; projecting the light off an angularly fixed input transfer mirror; projecting the light off an input scanner mirror; reflecting light off a metal film/sample array; transferring the reflected light using an output scanner mirror; transferring the reflected light off an output transfer mirror; detecting the reflected light using a detector; and identifying probes having a target molecule bound thereto; or identifying probes undergoing disassociation; or being enzymatically acted upon; wherein inter-molecular interaction is identified.

In some preferred embodiments, the input transfer mirror and the output transfer mirror are joined at congruent angles about the axis of the light beam. In still other preferred embodiments, the input transfer mirror and the output transfer mirror translate perpendicular to the light beam.

These and other features and advantages of various exemplary embodiments of the apparatus, devices and methods according to this invention are described in, or are apparent from the following detailed description of various exemplary embodiments of the method according to this invention.

BRIEF DESCRIPTION OF THE DRAWINGS

Various exemplary embodiments of the methods of this invention will be described in detail, with reference to the following figures, wherein:

FIGS. 6A and B represent another exemplary embodiment of the invention wherein the SPR apparatus is an angle-scanned SPR instrument, wherein FIG. 6A is a schematic diagram of the SPR apparatus and FIG. 6B is a representative spectrum derived therefrom;

FIGS. 7A and B represent another exemplary embodiment of the invention wherein the SPR apparatus is a wavelength-scanned SPR instrument, wherein FIG. 7A is a schematic diagram of the SPR apparatus and FIG. 7B is a representative spectrum taken therewith;

FIGS. 8A, B and C represent another exemplary embodiment of the invention wherein the SPR apparatus is an imaging SPR instrument, wherein FIG. 8A is a schematic diagram of the SPR apparatus, FIG. 8B illustrates an SPR image and FIG. 8C represents a difference image generated by the invention;

FIG. 9A is a are a schematic diagram of the SPR apparatus, FIGS. 10A, B and C represent another exemplary embodiment of the invention wherein the SPR apparatus is a wavelength-scanned imaging SPR instrument, wherein FIG. 10A is a schematic diagram of a wavelength-scanned imaging SPR instrument.

DETAILED DESCRIPTION OF THE EXEMPLARY EMBODIMENTS

Figure 1:
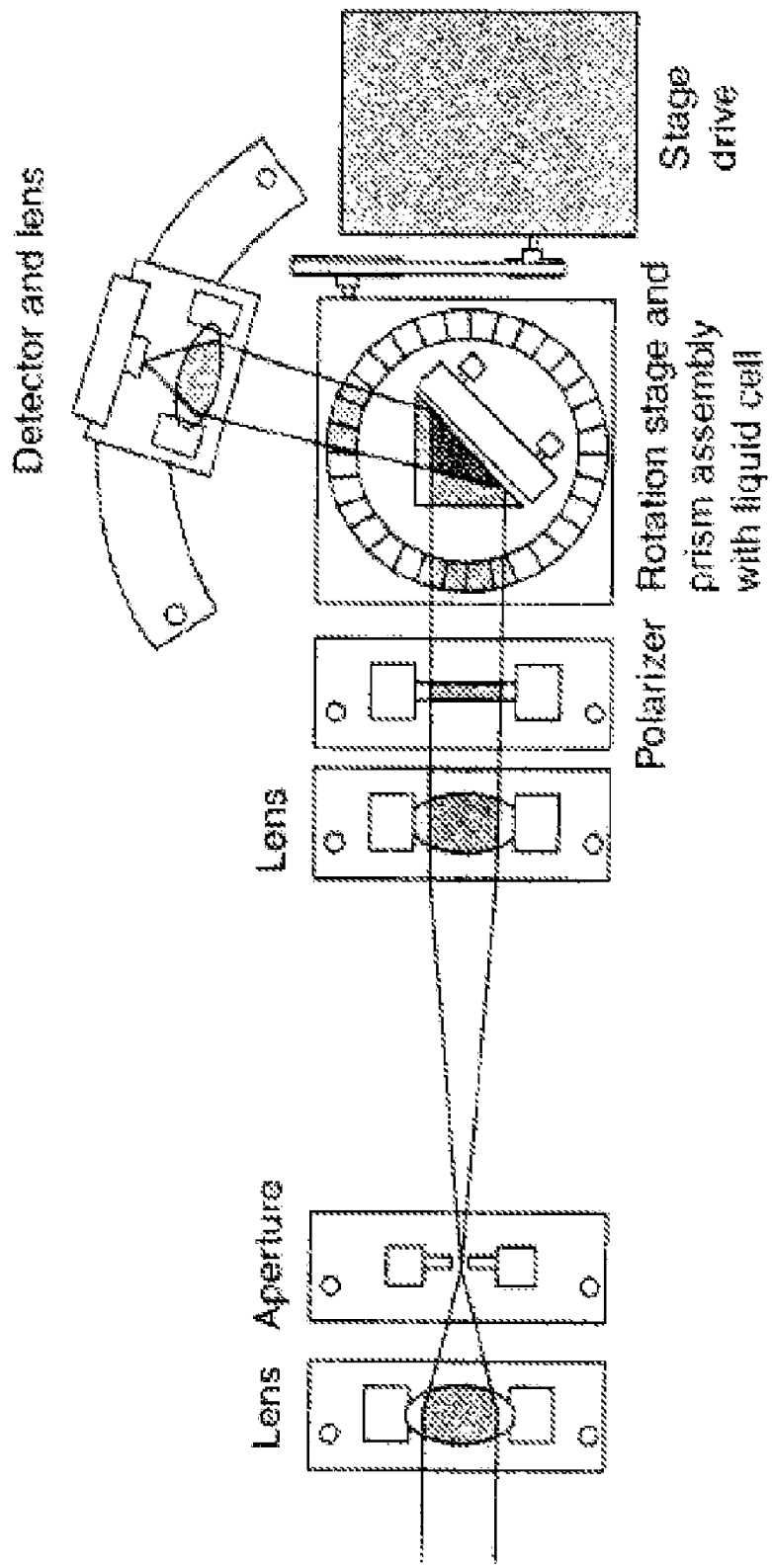
FIG. 1 is a top-plan view of an SPR device as known in the prior art.

Disclosed is a horizontal SPR sensor apparatus that provides a simplified beam path, ease of sample handling with concomitant ease of analysis. The horizontal SPR apparatus disclosed herein includes an input and output transfer mirror pair that translates vertically along an axis perpendicular to the beam path. The invention includes an input/output scanner mirror pair that is operatively linked to the transfer mirror pair. This allows for rotation of the scanner mirror pair in response to the vertical translation of the transfer mirror pair and maintains the incident light focus on the metal film/sample layer while varying the angle of incidence and thereby exciting the surface plasmon resonance at the thin metal film layer. Further, this allows the detector and detector optics to be fixed providing for the implementation of heavier multi-stage cooled detectors. Finally, the invention provides an SPR apparatus having a smaller footprint than known alternatives.

Before the present devices, apparatus, instruments and methods are described, it is to be understood that this invention is not limited to the particular devices, methods and protocols described, as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably. As used herein the term "sample array" means an individual sample or a plurality of samples that are aligned on a surface such that multiple SPR measurements are taken. Further as used herein, "sample" and "thin metal film" are used interchangeably to the extent that it is the sample that is placed on the thin metal film that results in the propagation of surface plasmon resonance waves on the surface of the thin metal film.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, optics, instruments, statistical analysis and methodologies which are reported in the publications which might be used in connection with the invention. Nothing herein is to be construed as an admission that the invention is not entitled to antedate such disclosure by virtue of prior invention.

In one exemplary embodiment, the invention provides a surface plasmon resonance instrument having a horizontal orientation. In this embodiment, the invention includes: input transfer optics, generating a light beam along a beam axis; an input transfer mirror joined to an output transfer mirror and translatable along an axis of symmetry such that the input transfer mirror and the output transfer mirror are symmetrically joined about the axis of symmetry. A first scanner mirror, rotatable about an axis is further included such that the first scanner mirror directs the beam to a sample. Also included is a second scanner mirror, rotatable about an axis parallel to the first scanner mirror and receiving light reflected from the sample and directing the light to the output transfer mirror. According to this design, the first scanner mirror and the second scanner mirror are operatively linked and operate in concert as the angle of incidence and angle of reflection are varied. A detector receives light from the output transfer mirror whereby the surface plasmon resonance response of a sample is measured.

In some exemplary embodiments of the invention, the input transfer mirror and the output transfer mirror are translationally joined at coequal angles around the beam axis such that the angle of the input beam equals the angle of the output beam. In other exemplary embodiments, the input scanner mirror and the output scanner each rotate around a point and are symmetrically opposable. In various exemplary embodiments, the light source may include, but is not limited to, broadband filaments, lasers, light emitting diodes, FT-IR spectrometers, fiber optic light sources and AOTF spectrometers. In some preferred embodiments, the detector is a single element sensor, an imaging detector or an element array detector. In still other embodiments, the detector includes a charged-coupled device camera and a central processing unit.

This invention separately provides a method of identifying inter-molecular interaction comprising placing a target molecule on a probe in a horizontally oriented surface plasmon resonance apparatus; directing a light beam to an input path in the horizontally-oriented SPR device; projecting the light off an input transfer mirror; reflecting the light off an input scanner mirror; reflecting light off a thin metal film/sample array; transferring the reflected light using an output scanner mirror; transferring the reflected light off an output transfer mirror; detecting the reflected light using a detector; and identifying probes having a target molecule bound thereto; or identifying probes undergoing disassociation; or being enzymatically acted upon; wherein inter-molecular interaction is identified.

In some preferred embodiments, the input transfer mirror and the output transfer mirror are joined at congruent angles about the axis of the light beam. In still other preferred embodiments, the input transfer mirror and the output transfer mirror translate along a path perpendicular to the input and output light beam.

Unlike most SPR analysis devices, the present invention provides an SPR analysis apparatus that allows for samples or thin films to be analyzed in the horizontal position. In addition, the design of the SPR apparatus allows for a simplified light path which further allows for the control of the incident light angle on the thin film for surface plasmon excitation. As shown, in this embodiment, the moveable elements consist of rotating symmetrical opposing mirrors and vertically translating opposing mirrors. For simplicity, the translating opposed mirror pair are simply a prism coated with a reflective surface. However, it should be appreciated that any opposed mirror pair are encompassed by the invention.

Figure 2:
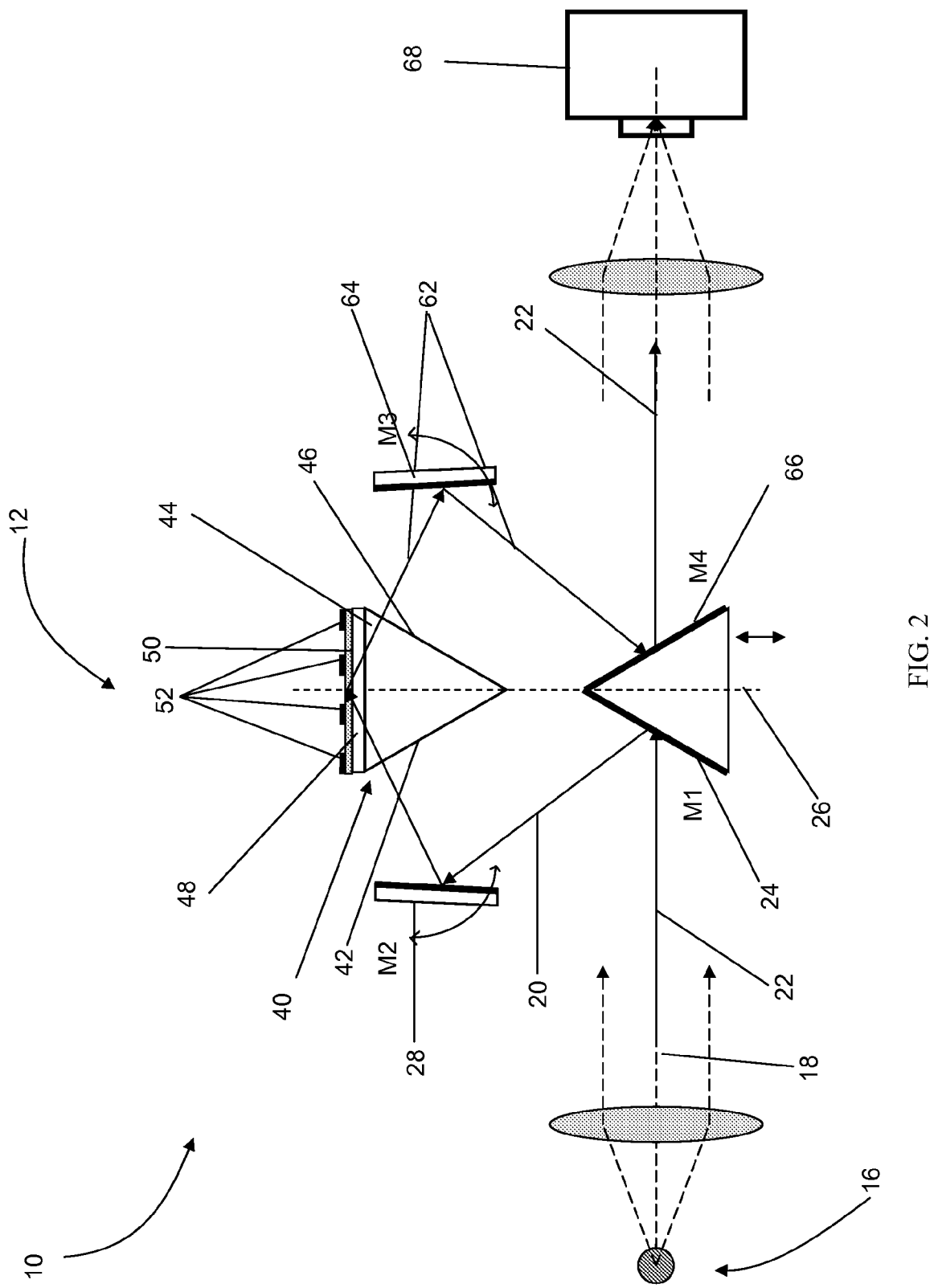
FIG. 2 is a schematic side-plan view of the light path according to one embodiment of the invention disclosed herein.

As shown in FIG. 2, a SPR device 10 according to the invention has an opto-mechanical interface 12 and a light beam 18 that begins with a light source 16 providing appropriate analyzing light as is well known in the art. See, for example, U.S. Pat. No. 6,330,062 (the '062 patent) which describes the use of a Michelson interferometer to provide a collimated light beam 18 suitable for inducing SPR waves. As shown, light beam 18 forms an incident ray 20 along a beam axis 22. The incident ray 20 strikes a translating input transfer mirror 24 and is reflected. Next, incident ray 20, strikes an input scanner mirror 28. The incident ray 20 is then reflected to a prism 40 passing through a first prism face 42, a second prism face 44 and internally reflected at a thin metal film 50 and/or a sample film 52. Contact of the incident ray 20 with the sample film 52 and thin film 50 results in a surface plasmon resonance reflected ray 62 from the sample film reflecting through a third prism face 46 to strike an output scanner mirror 64. The reflected ray 62 then strikes an output transfer mirror 66 to reenter the beam axis 22 and proceed to an output detector optics 68. Such output optics are well known in the art such as those, for example, described in the '062 patent. In such embodiments the detector optics may include without limitation a CCD camera or a linear array detector. However, it should be appreciated that any type of detector capable of measuring surface plasmon resonance is contemplated.

It will be appreciated, by those of skill in the art, that the light source can be any suitable light source including, but is not limited to, a Michelson interferometer. For example, suitable light sources include, without limitation: a laser, a tunable-diode laser, a monochromatic light source, an FT-IR spectrometer, a light-emitting diode (LED), a broadband filament, an AOTF spectrometer, a fiber optic light source and a dispersive spectrometer. As disclosed herein, the apparatus 10 according to the invention has a fixed input light source 16, an opto-mechanical interface 12, including, a fixed prism element 40 and a horizontally orientated thin metal film 50/sample film 52, such as, for example an SPR chip, and a fixed detector stage 68. The moveable elements consist of rotating symmetrical opposing scanner mirrors 28 and 64 and vertically translating and symmetrically opposing input and output transfer mirrors 24 and 66. However, it should be appreciated that while, in the exemplary embodiments described herein, the translating opposed transfer mirrors 24 and 66 are symmetrically joined about the axis of symmetry 26 in other exemplary embodiments the transfer mirrors are a prism with mirrored or reflective faces. Such prisms are commercially available from, for example, Edmund Optics (Barrington, N.J.). Further, it will be appreciated, by those of skill in the art, that while the SPR device 10 described herein can be used in a horizontal position, the instrument can be turned 90° to allow the device to be used in a vertical position.

Figure 3:
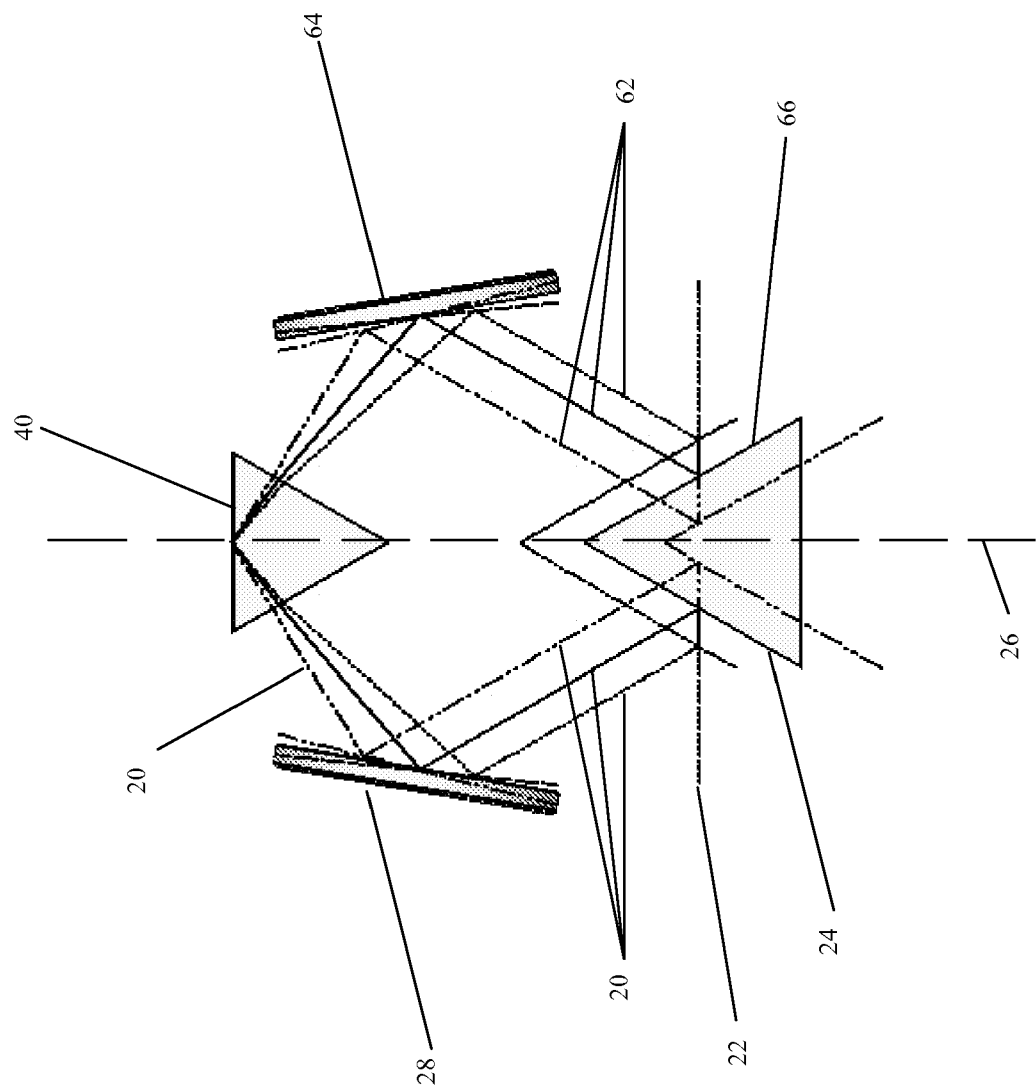
FIG. 3 is a schematic side-plan view of the light-path as the angle of incidence is varied over three values according to the embodiment of the invention shown in FIG. 2.

Referring again to FIGS. 2 and 3, it should be noted that the input and output scanner mirrors 28 and 64 are rotatable and designed and configured to move in tandem with each other. As shown in FIG. 3, the angle of incidence θ is varied by translating input transfer mirror 24 vertically and rotating scanner mirror 28 to maintain focus of the incident ray 20 on the thin metal film/sample 50/52. The reflected beam 62 is tracked by the rotation of output scanner mirror 64 complementary to input scanner mirror 28. The vertical translation of output transfer mirror 66 in concert with input transfer mirror 24 allows the reflected ray 62 to reenter the path of the beam axis 22. Using this arrangement, as the incident angle θ is varied; the light beam at the metal film is fixed. This solution allows the output detector optics and detector to be stationary thereby alleviating the need to rotate the detector position to track the reflected ray 62.

FIG. 3 illustrates the change in the beam path 20/62 as the angle of incidence is varied over three values. As shown, the vertical translation of the transfer mirror pair 24/66 shifts the position at which the incident ray 20 strikes scanner mirror 28. Scanner mirror 28 is correspondingly rotated proportional to the translation of the input transfer mirror 24 maintaining the position at which incident ray 20 hits the sample 52 (not shown) while changing the angle of incidence at which the incident ray 20 strikes the sample 52 at that position. By physically linking the transfer mirror pair 24/66 with the scanner mirror pair 28/64 the input geometry equals the output geometry, and the incident ray 20 position on the metal film 50 remains constant as mirrors 24 and 66 translate along an axis of symmetry 26 normal to the beam axis 22. Further, as shown, because symmetrical transfer mirrors 24 and 66 move in unison, the motion of scanner mirrors 28 and 64 necessary to maintain the focus of the incident ray and the reflected ray is also symmetrical and in unison. Thus, disclosed are optics necessary to provide a reflected ray 62 that reenters the beam axis 22 allowing for a stationary detector and further allowing for the horizontal orientation of the sample. Those of skill in the art will appreciate that the design disclosed herein also allows for a much more facile orientation in a smaller and more convenient foot-print. However, it should be appreciated that it may be desirable to rotate the device 90° thereby providing the device according to the invention with a vertical orientation.

As illustrated in FIG. 2, input light is reflected from mirror 24 to mirror 28 and from mirror 28 is directed to the first prism face 42, is then incident at the thin metal film 50 and the sample 52 which is located at the second prism face 44 of the SPR prism 40. The reflected ray 62 then passes through the third prism face 46 to the output scanner mirror 64, and directed to output transfer mirror 66, which reflects the output ray 62 to detector optics and a detector system 68.

Figure 4:
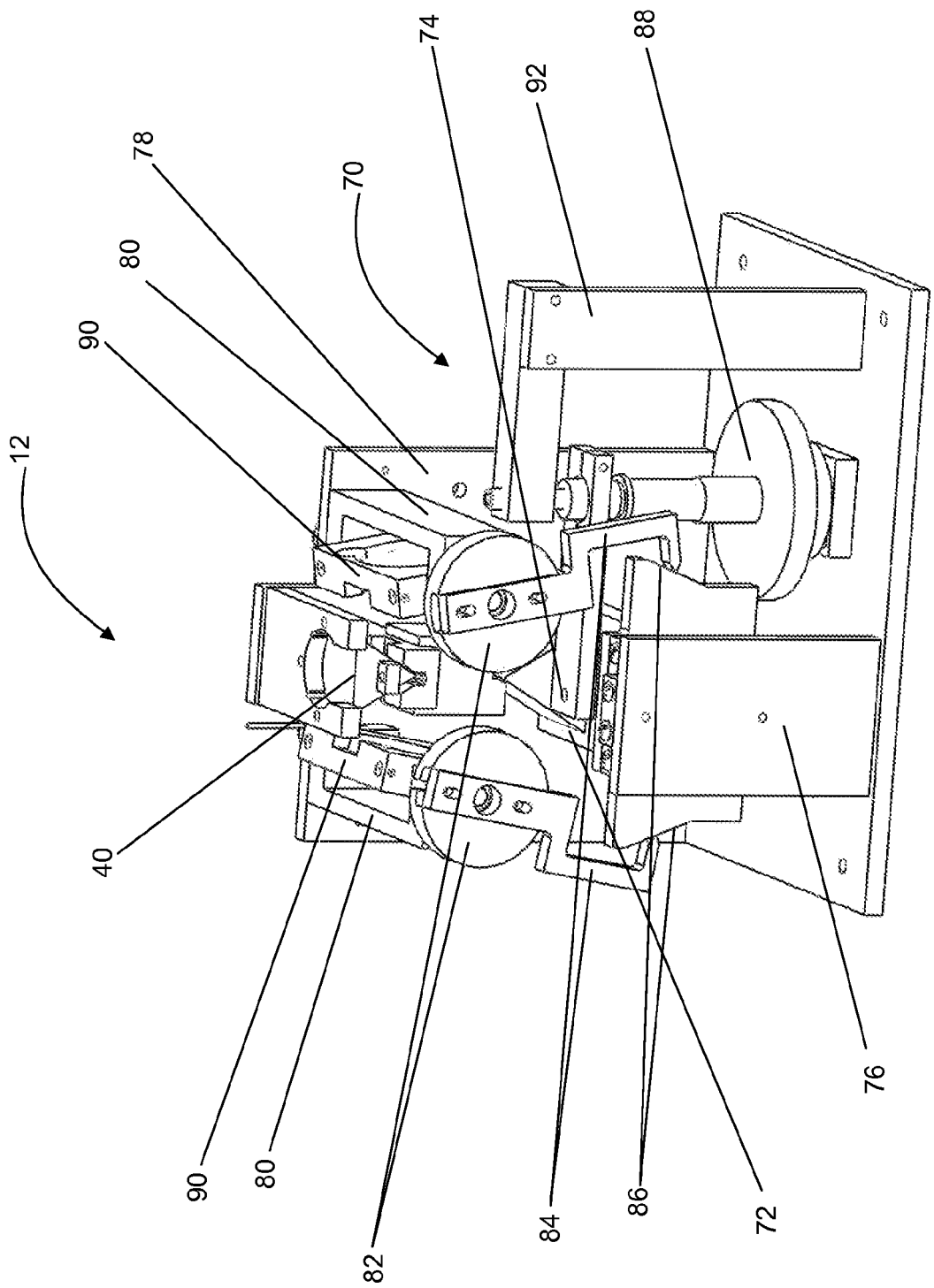
FIG. 4 is a front perspective view of the SPR apparatus according to the embodiment shown in FIG. 2.
Figure 5:
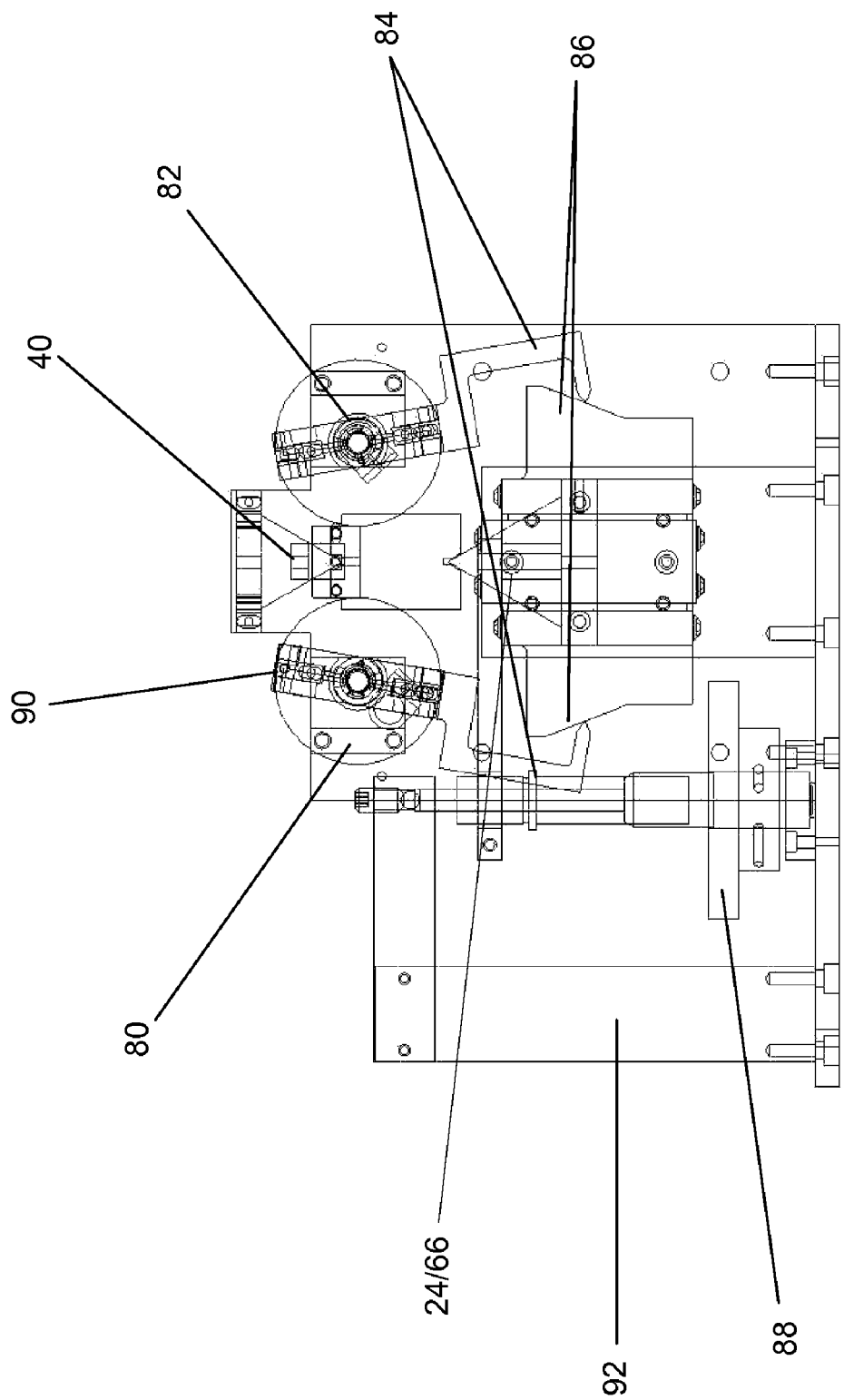
FIG. 5 is a rear view of the embodiment of the invention shown in FIG. 4.

FIGS. 4 and 5 illustrate the mechanical connectivity of the horizontal surface plasmon resonance device described herein. As shown in FIG. 4, the transfer mirror pair 24/66 and the scanner mirror pair 28/64 are connected through a cam linkage 70. In the embodiment shown, the cam linkage 70 includes mounting brackets 76/78 which support the cam linkage 70. Further shown is a transfer mirror mount 72 upon which mirror pair 24/66 are located. A vertical mount 92 supports a vernier 88, which translates a linear bearing 74, and is connected to the mirror mount 72 thereby providing for vertical translation of the mirror mount 72. Further attached to linear bearing 74 are symmetrical cam surfaces 86 which are partially triangular as shown. In the exemplary embodiment of the invention shown in FIGS. 4 and 5, an opposing mounting bracket 78 has symmetrical, fixed, axial mounts 80 to which are attached spring loaded cams 82 which also include mounts 90 for scanner mirrors 28/64. Further, attached to the cams 82 are calipers 84. The calipers 84 are designed and configured such that the calipers 84 translate along triangular cam surfaces 86 thereby rotating the scanner mirrors in response to the vertical translation of transfer mirror mount 72. By linking transfer mirror mount 72 and cam surfaces 86 to the vernier 88 the cams 82 automatically rotate mirror mounts 90 in coordination with the translation of the transfer mirrors 24/66. This allows the scanner mirrors 28/64 to each rotate about an axial point, the two points forming an axis, which is parallel to the beam axis 22 and normal to the axis of symmetry 26, thereby providing a closed system by which rotation of the scanner mirrors 28, 64 is directly related to the translation of transfer mirrors 24 and 66.

As will be apparent to those of skill in the art, the angle of incidence θ of light beam 20 on the sample 52 is varied by rotating scanner mirror 28. To maintain the incident ray 20 position on the SPR sample 52, the location of the incident ray 20 on mirror 28 must be shifted. This is accomplished by vertical translation of transfer mirror 24. For example, as illustrated in FIG. 3, if a smaller angle of incidence is desired, transfer mirror 24 translates upward, which shifts the light beam position downward on scanner mirror 28. Scanner mirror 28 is then simultaneously rotated the corresponding amount in a counter-clockwise direction. If a larger angle of incidence is desired, transfer mirror 24 translates downward, which shifts the incident ray 20 position upward on scanner mirror 28. Scanner mirror 28 is simultaneously rotated the corresponding amount in a clockwise direction. As shown in FIGS. 4 and 5, in one preferred embodiment, the vernier 88 is manually operated however; it should be appreciated that the cam linkage 70 can be operated by any convenient method such as, for example, via a step motor, push rod or the like. Further, it should be appreciated that while the exemplary embodiment shown is designed to adjust the mirror positions by having the translating mirror pair 24/66 drive the cam/caliper 86/84 linkage which rotates the scanner mirrors 28/64, it is well within the scope of the invention to have the rotating scanner mirror pair 28/64 drive mechanical linkage to translate the mirror pair 24/66.

Those of skill in the art will appreciate that, in various exemplary embodiments, a single control mechanism causes the movement of the transfer mirrors 24/66 which controls the angle of incidence θ as illustrated in FIGS. 4 and 5. In some preferred embodiments this control is accomplished with a vernier 88 coupled to the transfer mirrors 24/66 and then coupled to the rotating scanner mirrors 28/64 via a cam linkage 70. Alternatively, in other exemplary embodiments, the single control can be connected to scanner mirrors 28/64 and then coupled to the transfer mirror pair 24/66 by a coupling and gear linkage as is well known by those of skill. Further, it should be appreciated that, while the use of prism 40 allows for proper surface plasmon resonance, a grating-coupled configuration could be utilized as well in the horizontal SPR device disclosed herein. In this embodiment, a metal-coated grating replaces the prism/thin metal film and in some embodiments would face downwards. In various exemplary embodiments of the invention using a grating, a flow cell is mounted to the grating and includes inlet/outlet windows for the incident beam and the reflected beam. Further, in other exemplary embodiments, the metal-coated grating is exposed to probe molecules and then further exposed to target analyte for purposes of identifying inter-molecular interaction and/or surface changes resulting from the action of an enzyme.

FIGS. 6A and 6B illustrate one exemplary embodiment of the invention comprising an angle-scanned SPR instrument. In this embodiment, as illustrated in FIG. 6A, the light source is a monochromatic light source. In this embodiment, the wavelength is held constant and the incident angle is scanned. Those of skill in the art will appreciate that, this design results in an angle-scanning SPR wherein the reflected light is measured as a function of incident light angle at a fixed incident light wavelength. FIG. 6B is a representative spectrogram generated by an angle-scanning SPR. The two curves represent the measured light intensity as a function of incident angle on the thin metal film 50/sample surface 52, before and after target analyte binding to the sample surface.

Figure 7A:
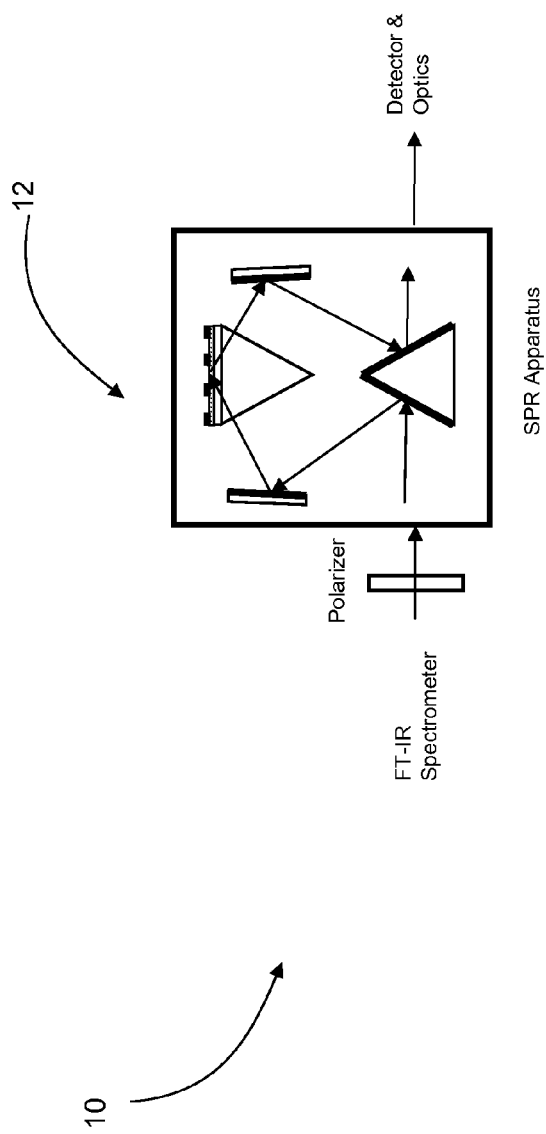
Figure 7B:
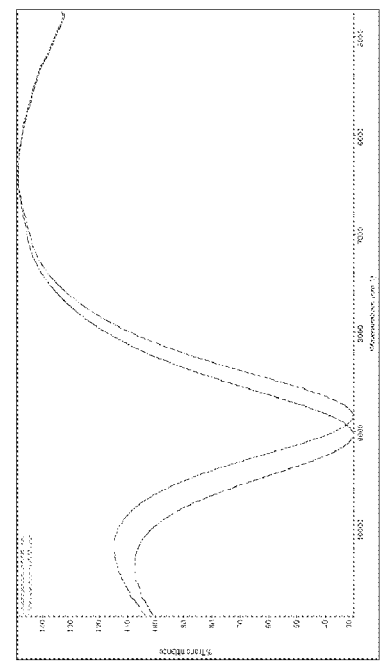

FIGS. 7A and 7B illustrate another exemplary embodiment of the invention comprising a wavelength scanned SPR instrument. In this embodiment, the light source is tunable, such as with an FT-IR spectrometer as shown in FIG. 7A. FIG. 7B shows two representative spectra in which the reflected light intensity is measured as a function of the change in incident wavelength, before and after target analyte binding to the sample surface 52. Thus, those of skill in the art will appreciate that the invention can be utilized for a wavelength-scanning SPR wherein the reflected light is measured as a function of incident light wavelength at a fixed incident light angle.

FIGS. 8A, B and C illustrate yet another exemplary embodiment of the invention comprising an imaging SPR apparatus. In this embodiment, represented diagrammatically in FIG. 8A, the light source is a monochromatic light source. In this embodiment, the reflected light is measured as a function of spatial position on the thin metal film 50 at a fixed incident light wavelength and a fixed incident light angle. FIG. 8B shows a representative image from an SPR imaging apparatus. In this example, the difference image FIG. 8C was obtained by subtracting the images taken before and after exposing the array to a nucleotide sequence that is complementary to an immobilized target sequence. It will be appreciated by those of skill in the art that such imaging is not limited to nucleotides but to any receptor/ligand pair.

Figure 9A:
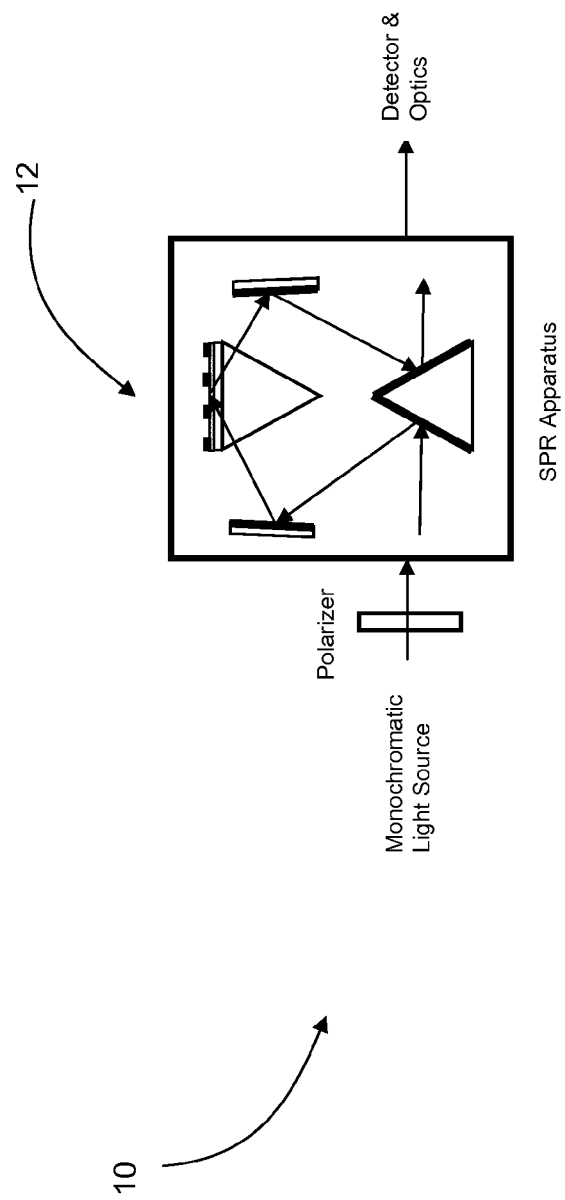
FIGS. 9A, B and C represent another exemplary embodiment of the invention wherein the SPR apparatus is an angle-scanned imaging SPR instrument.
Figure 9C:
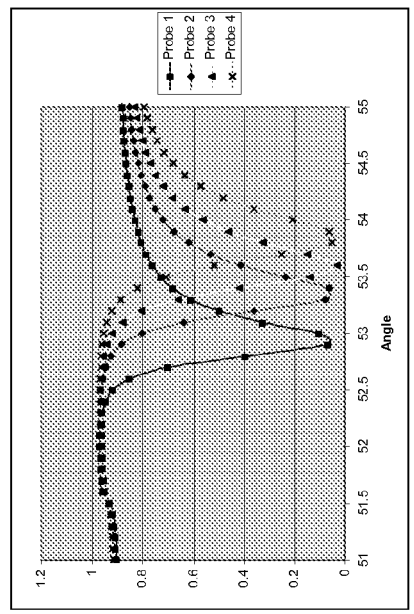
FIG. 9B illustrates a simple sample array and FIG. 9C is a representative spectra obtained therefrom.
Figure 9B:
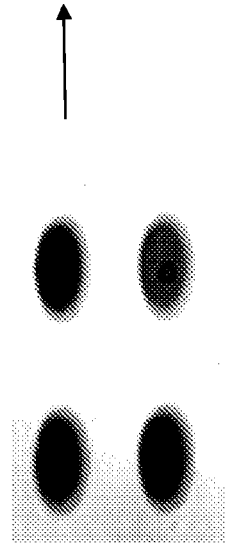

FIGS. 9A, B and C illustrate another exemplary embodiment of the invention comprising an angle-scanned imaging SPR apparatus. As shown, in this embodiment the light source is a monochromatic light source that is used by the SPR apparatus. FIG. 9C shows a representative spectrogram resulting from the scanning of the four probes placed on the array shown in FIG. 9B. This embodiment will produce multiplexed angle-scanned reflectivity measurements for discrete spatial areas on the thin metal film 50/sample surface 52.

Figure 10A:
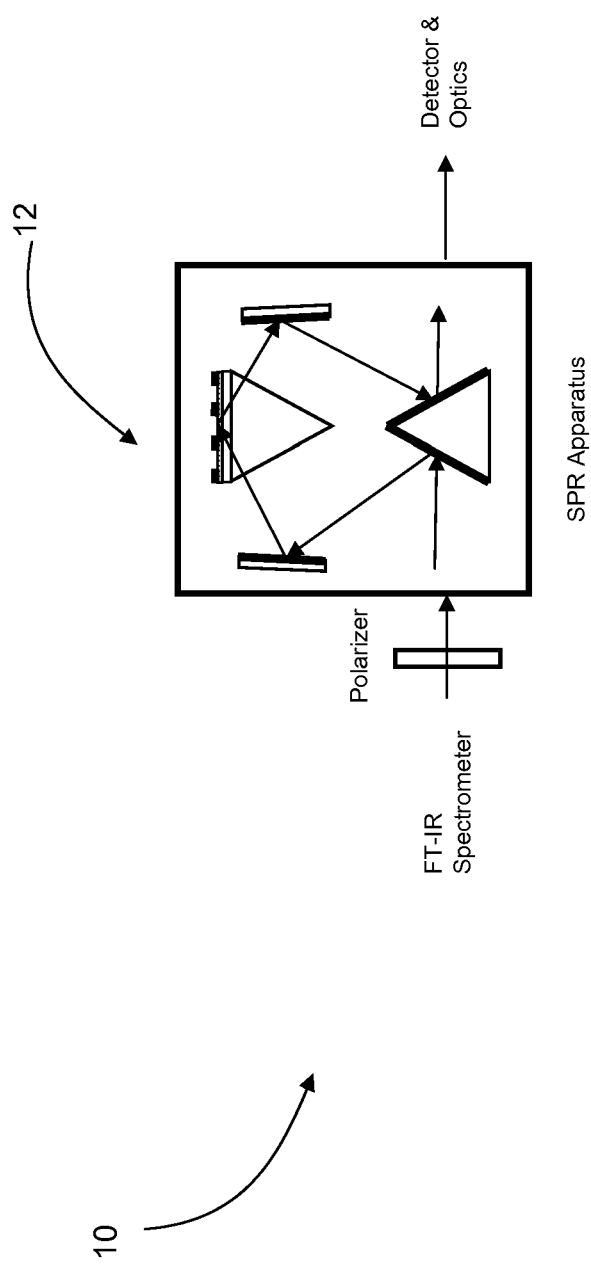
Figure 10C:
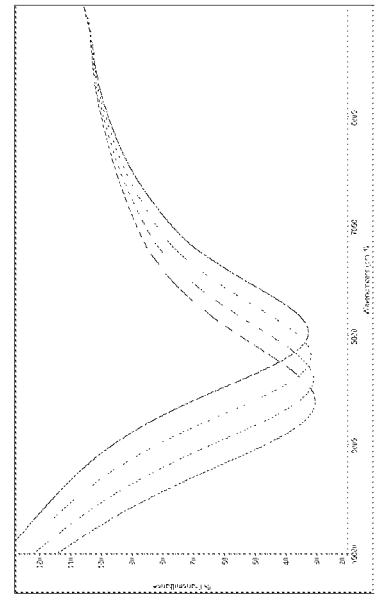
FIG. 10B illustrates a simple sample array and FIG. 10C is a representative diagram of the shift in wavelength recorded therefrom.
Figure 10B:
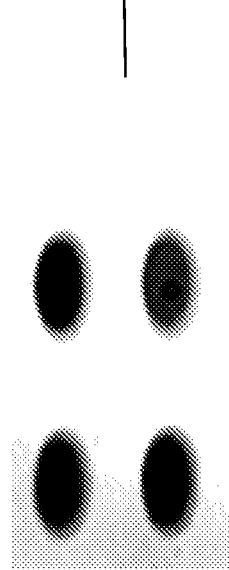

FIGS. 10A, B and C illustrate yet another exemplary embodiment of the invention comprising a wavelength-scanned imaging SPR apparatus. As shown schematically in FIG. 10A, in this embodiment, the light source is tunable, such as, for example, that provided by an FT-IR spectrometer. FIG. 10B illustrates an array having four probes applied thereon. FIG. 10C is a spectrogram illustrating the simultaneous measurement of the wavelength-dependent reflectivity of the four probes on the thin metal film 50/sample surface 52.

While various instrument configurations utilizing the SPR horizontal apparatus are depicted, the intended configurations are not restricted to the specific embodiments illustrated herein. As disclosed the apparatus is intended for use over a range of wavelengths and incident angles, with a variety of thin metal film surfaces. For example, the invention is amenable to use with various light sources such as, but not limited to, broadband filaments, laser, light emitting diodes, FT-IR spectrometers, fiber optic light sources and AOTF spectrometers. Further, according to the invention, the light path can be processed with various optical elements including, but not limited to, polarizers, band-pass filters, dispersive spectrometers and liquid crystal retarder devices. In addition, in various exemplary embodiments, the detector can be, for example, a single element sensor, an imaging detector, or an array of single element sensors.

While this invention has been described in conjunction with the various exemplary embodiments outlined above, various alternatives, modifications, variations, improvements and/or substantial equivalents, whether known or that are or may be presently unforeseen, may become apparent to those having at least ordinary skill in the art. Accordingly, the exemplary embodiments according to this invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents of these exemplary embodiments.

What is claimed is:

1. A surface plasmon resonance sensor apparatus having a horizontal metal film orientation comprising:
    a) input transfer optics generating a light beam along a beam axis;
    b) an input transfer mirror joined to an output transfer mirror and translatable along an axis of symmetry perpendicular to the beam axis, wherein the input transfer mirror and the output transfer mirror are symmetrically joined about the axis of symmetry;
    c) the input transfer mirror directing light to a first scanner mirror;
    d) a first scanner mirror rotatable about an axis and wherein the first scanner mirror directs the beam to a surface which is one of a prism, a metal film surface and a thin film surface;
    e) a second scanner mirror rotatable about an axis parallel to the first scanner mirror and receiving light reflected from the surface and directing the light to the output transfer mirror, wherein the first scanner mirror and the second scanner mirror are operatively linked and each rotate on an axis perpendicular to the beam axis; and f) detector optics and a detector receiving light from the output transfer mirror; whereby the surface plasmon resonance response of a sample is measured.

2. The surface plasmon resonance sensor apparatus of claim 1, wherein the input transfer mirror and the output transfer mirror are symmetrically joined at coequal angles around the axis of symmetry such that the angle of the input beam equals the angle of the output beam.

3. The surface plasmon resonance sensor apparatus of claim 1, wherein the input scanner mirror and the output scanner mirror are symmetrically disposed about the axis of symmetry.

4. The surface plasmon resonance sensor apparatus of claim 1, wherein the light source is selected from the group consisting of: a laser, a tunable-diode laser, a monochromatic light source, a light-emitting diode (LED), an FT-IR spectrometer, a broadband filament, an AOTF spectrometer, a dispersive spectrometer, and the output of a fiber optic cable.

5. The surface plasmon resonance sensor apparatus of claim 1, wherein the detector is a single element sensor, an imaging detector or a multi-element array detector.

6. The surface plasmon resonance sensor apparatus of claim 5, wherein the detector includes a charged-coupled device camera and a central processing unit.

7. The surface plasmon resonance sensor apparatus of claim 1, wherein the angle of light incidence is varied by vertically translating the first transfer mirror and rotating the first scanner mirror.

8. The surface plasmon resonance sensor apparatus of claim 1, wherein the transfer mirror pair and scanner mirror pair are linked via a mechanical assembly to cause the output mirror pair to move in symmetrical concert with the input mirror pair.

9. The surface plasmon resonance sensor apparatus of claim 1, wherein the instrument is an angle-scanned surface plasmon resonance instrument, a wavelength-scanned surface plasmon resonance instrument, an imaging surface plasmon resonance instrument, an angle-resolved imaging surface plasmon resonance instrument or a wavelength-resolved imaging surface plasmon resonance instrument.

10. The apparatus of claim 1, wherein the apparatus is rotated 90 degrees from the horizontal plane to orient the sample in the vertical orientation.

* * * * *